Figure 1:
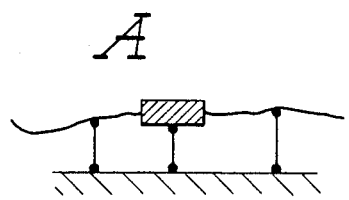
Figure 1:
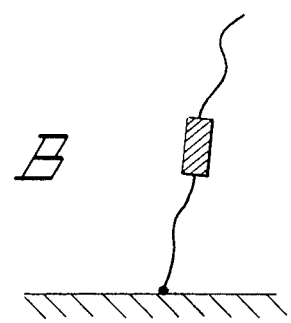

United States Patent [19]

Larm

[11] Patent Number: 4,613,665

[45] Date of Patent: Sep. 23, 1986

[54] PROCESS FOR COVALENT COUPLING FOR THE PRODUCTION OF CONJUGATES, AND POLYSACCHARIDE CONTAINING PRODUCTS THEREBY OBTAINED

[76] Inventor: Olle Larm, Nyängsvägen 86, S-161 39 Bromma, Sweden

[21] Appl. No.: 464,996

[22] Filed: Feb. 8, 1983

[30] Foreign Application Priority Data

Feb. 9, 1982 [SE] Sweden ................................ 8200751

[51] Int. Cl.[4] ........................ C08B 37/08; C08B 37/10
[52] U.S. Cl. ..................................... 536/20; 525/54.2; 536/21; 536/55.1; 536/55.3
[58] Field of Search ................. 536/20, 21, 55.1, 55.3; 260/112 R; 525/54.2

[56] References Cited

U.S. PATENT DOCUMENTS

| | | | |
|---|---|---|---|
| 2,016,962 | 10/1935 | Flint et al. | 536/55.3 |
| 2,918,462 | 12/1959 | Druey et al. | 536/55.3 |
| 3,673,612 | 7/1972 | Merrill et al. | 536/21 |
| 3,826,678 | 7/1974 | Hoffman et al. | 260/9 |
| 3,947,352 | 3/1976 | Cuatrecasas | 536/55.1 |
| 4,118,485 | 10/1978 | Eriksson et al. | 536/21 |
| 4,301,067 | 11/1981 | Koshugi | 536/20 |
| 4,329,383 | 5/1982 | Joh | 428/36 |
| 4,424,346 | 1/1984 | Hall et al. | 536/20 |

FOREIGN PATENT DOCUMENTS

| | | |
|---|---|---|
| 2250795 | 6/1975 | France . |
| 2309245 | 11/1976 | France . |
| 365710 | 4/1974 | Sweden . |
| 400173 | 3/1975 | Sweden . |
| 2041377 | 9/1980 | United Kingdom . |

OTHER PUBLICATIONS

Biochemistry, vol. 15, No. 18, pp. 3932–3942, Shively et al.

J. Appl. Physiol. 29(5): 723–730, 1970.

Primary Examiner—Johnnie R. Brown
Attorney, Agent, or Firm—Burns, Doane, Swecker & Mathis

[57] ABSTRACT

A process to produce by covalent binding conjugates of a substance containing a 2-amino-2-deoxyglycopyranosyl residue the $NH_2$-function of which in its most stable conformation is equatorially oriented, and a substrate containing a primary amino group. This is done by subjecting the substance to degradation by diazotation to form a substance fragment having a free terminal aldehydo group, said fragment through its aldehydo group being reacted with the amino group of the substrate to form a Schiffs base which is then by reduction converted to a secondary amine.

The substance is preferably selected from oligo and polysaccharides containing glucosamine or galactose amine units. The substrate is suitably selected from surface-aminated plastic objects, aminated gels and proteins.

The conjugate described consists of a 1-deoxy-2,5-anhydrohexitol unit which constitutes terminal unit in an oligo or polysaccharide and which in 1-position is covalently bound to an amino group associated with a substrate.

9 Claims, 3 Drawing Figures

▨ = active sequence

PROCESS FOR COVALENT COUPLING FOR THE PRODUCTION OF CONJUGATES, AND POLYSACCHARIDE CONTAINING PRODUCTS THEREBY OBTAINED

The present invention relates to a new process to produce by covalent binding conjugates of a substance containing a 2-amino-2-deoxyglycopyranosyl unit and a substrate containing primary amino groups.

In different contexts it is of interest to bind organic substances, mainly oligomeric and polymeric substances, to substrates of different types. Such substrates can be constituted by plastic surfaces, for example for binding heparin to medical instruments to provide for anti-coagulation effect, they may be proteins, for example for preparing neoglycoproteins (synthetic glycoproteins) for cell stimulation, preparation of antigenic determinants etc., or they can be constituted by for example gels for affinity chromatography. In this connection it is an essential advantage if the binding can be provided with a high degree of specificity. The biological activity of the substance to be coupled to the substrate and the properties of the latter shall not be considerably changed.

Thus, the present invention relates to coupling of organic substances to substrates of different types, the common denominator of the substrates being the fact that they contain primary amino groups. The invention will be exemplified mainly with reference to polysaccharides, particularly those possessing biological activity, but it should be observed that this exemplification only is intended to be illustrative and not limiting. There are mainly four high-molecular organic substances which are exemplified, namely heparin, hyaluronic acid, dermatan sulphate and chitosan. The chemical structure of said four substances will now be briefly discussed.

Heparin (ref. 1)

Heparin is built up from alternating glycuronic acid and glucosamine units. The glycuronic acid units consist of D-glycuronic acid and L-iduronic acid. These are respectively $\beta$- and $\alpha$-(1,4)-bound to the D-glucosamine units. A large proportion of the L-iduronic acid residues are sulfated in the 2-position. The D-glucosamine units are N-sulfated, sulfated in the 6-position and are $\alpha$-(1,4)-bound to the uronic acid residues. Certain D-glucosamine units are also sulfated in the 3-position.

Hyaluronic acid (ref. 2)

Hyaluronic acid is composed of alternating 1,4-bound $\beta$-D-glucuronic acid and 1,3-bound N-acetyl-$\beta$-D-glucosamine units.

Dermatan sulfate (ref. 1)

Dermatan sulfate is composed of alternating L-iduronic acid and N-acetyl-D-galactosamine units which are respectively $\alpha$-(1,3)- and $\beta$-(1,4)-bound. The polysaccharide is partially O-sulfated.

Chitosan (ref. 3)

Chitosan is built up from $\beta$-(1,4)-bound D-glucosamine residues.

Heparin imparts its blood-anticoagulating effect by activating the plasma protein antithrombin (AT) (ref. 4). Activated AT inhibits a number of serine proteases in blood (factor X ($X_a$) thrombine . . . ). By the present invention there is provided a new method for covalent coupling of heparin to AT. This produces a permanently activated AT which in in vivo systems has a thrombosis preventing effect, causes reduced hemorrhage risks and has a longer half life than heparin.

According to conventional technique antithrombin is isolated from blood plasma by affinity chromatography on heparin-Sepharoses (ref. 5). The methods heretofore used to bind heparin to gels have, however, resulted in the heparin losing a significant part of its activity. With regard to this activity of the heparin it is only a small part of the heparin molecule, namely an active sequence having the structure→4)-$\alpha$-L-IdAp-(1→4)-$\alpha$-D-Glc-NAcp-(1,4)-$\beta$-D-GlcAp-(1→4)-$\alpha$-D-GlcNSO$_3$p-(1→4)-$\alpha$-L-IdAp-2OSO$_3$-(1→4)-$\alpha$-D-GlcNSO$_3$⁻p-(1→4)-$\alpha$-L-IdAp-2-OSO$_3$⁻(1→, which has affinity to antithrombin. (Ref. 6). In this sequence most of the glucosamine entities are 6-sulfated and one of them carries a 3-sulfate group. By applying the technique of the present invention one can bind a considerably greater quantity of antithrombin per mole of immobilized heparin than in conventional heparin gels.

It is well known that when blood comes into contact with other materials than the fresh natural wall of the blood vessel, for example in surgery with medical instruments, the use of heart-lung machines etc., activation of certain circulating cells and enzyme systems takes place which inter alia results in coagulation of the blood (ref. 7). If such coagels or thrombi are formed on surfaces which are in contact with the blood flow there is great risk that they will be released and cause serious circulation disturbances, so-called thrombosis. Fargoing efforts have been made in order to find materials of reduced tendency to form thrombosis. The technique that up to now has given the most promising results has consisted in coating the foreign surface with heparin (ref. 7).

Three principally different methods of binding heparin have been tested up to now. Heparin which simply can be described as a polymer anionic compound, easily forms water-insoluble ion complexes with cation compounds, a fact which has been used for the production of surface-bound ion complexes of heparin, (ref. 7). A decisive disadvantage of such processes is, however, the fact that ion complexes with heparin are unstable when contacting the blood in view of which the effect will be of short duration. In order to avoid rapid dissolution one has tried different methods of binding heparin with stable covalent bonds. The attempts made up to now along this route have not led to the desired result but as a rule the biological activity of the heparin has been lost. A third method consists in first preparing a surface-bound ion complex, see Canadian Pat. No. 948,105, which is then stabilized by chemical reduction with glutar dialdehyde. A heparin surface prepared by the last-mentioned method has verified non-trombogenic properties. However, a small quantity of heparin will be released during an initial phase when contacting blood.

By covalent coupling of hyaluronic acid to plastic implants for for example eye surgery the implants can acquire better tissue affinity. In this manner one avoids complementary activation and activation of the mononuclear cell system which is part of the defense of the body against external attack. The present invention enables effective and easy coupling of hyaluronic acid to solid materials, such as plastics and metals.

In biological material miniscule change of the structure of an active sequence of the material results in loss of the relevant activity. Particularly as regards the heparin the active sequence as previously described is easy to effect, for example when coupling the heparin to a substrate, and the invention has inter alia for its purpose to provide a coupling technique, the use of which means that the biological activity will be maintained.

In principle, polysaccharides can be linked to a surface in two different ways which are illustrated in the appended FIG. 1 with FIGS. A and B.

The methods heretofore used for covalent coupling of polysaccharides to different substrate surfaces have been of general type, i.e. the cross-linking reagent has had the possibility of reacting with functional groups arbitrarily localized along a given polysaccharide chain (FIG. 1 A). With the highest probability a possible active sequence will in this case be involved in the coupling, the biological activity being lost. According to the invention there is provided a technique which enables coupling in accordance with what has been illustrated in FIG. 1 B whereby the biological activity can be maintained.

The present invention has thus for its object to provide a process for covalent binding of oligomeric or polymeric organic substances to substrates of different types containing primary amino groups. The invention relates in particular to a new technique for coupling oligo or polysaccharides to substrates.

For this purpose the process of the present invention is characterized thereby that the substance to be coupled is subjected to degradation by diazotation to form a substance fragment having a free terminal aldehyde group. The substance fragment is then brought to react through its aldehydo group with the amino group of the substrate to form a Schiffs' base which then by reduction is converted to a secondary amine.

Figure 2:
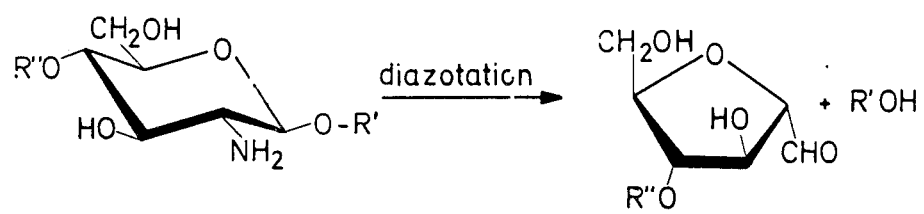

As previously mentioned the substance to be coupled to the substrate contains a 2-amino-2-deoxyglycopyranosyl residue the $NH_2$-function of which in the most stable conformation is equatorially oriented. In connection with the degradation this entity is diazotized and converted to a terminal 1-deoxy-2,5-anhydrohexitol entity. The diazotizing reaction can be illustrated with the reaction equation according to FIG. 2 on the appended drawing.

The substance is thus partially degraded and a reactive aldehyde group is provided at the reducing end. The formed substance fragment with the terminal aldehyde group is then reacted with a substrate containing primary amino groups. The reaction can take place in water at pH 3-7 or within the same pH-range in a suitable organic solvent, for example formamide or dimethyl sulphoxide. By this reaction instable Schiffs' bases are formed. These are then by reduction with a suitable reducing agent, for example a cyanoborohydride, preferably of an alkali metal, such as sodium, potassium or lithium, converted to form stable secondary amines. (Ref. 8).

The diazotation is suitably performed in an aqueous solution with a suitable diazotizing agent, for example a nitrite, such as sodium nitrite, in acid solution or butyl nitrite. While the invention is not limited to any particular theory it is assumed that the diazotation is provided by the formation of $NO^+$-ions, in view of which the diazotation is thus suitably performed with an agent capable of forming such ions.

Among preferred substances for coupling to the substrate there may be mentioned oligo or polysaccharides containing glucosamine or galactosamine entities. Said substances are preferably selected from heparin and heparin derivatives, at least partially deacetylated dermatan sulfate, chitosan and at least partially deacetylated hyaluronic acid.

Among substrates there may be mentioned plastic surfaces containing primary amino groups, for example plastic objects to which it is desirable to impart a non-thrombogenic surface, aminated gels and proteins.

According to a further aspect of the present invention there is provided a conjugate formed from the said substance and a substrate. This conjugate consists of an 1-deoxy-2,5-anhydrohexitol entity which constitutes a terminal entity in a polysaccharide and which in the 1-position is covalently bound to an amino group associated with the substrate. The hexitol entity contained in the conjugate is preferably a mannitol entity. The polysaccharide is preferably derived from heparin, hyaluronic acid or from chitosan. Alternatively, the hexitol entity is a talitol entity, the polysaccharide being derived from for example dermatan sulfate.

In the following the invention will be illustrated by non-limiting examples.

DIAZOTATION OF GLUCOSAMINOGLYCAN HAVING FREE AMINO FUNCTIONS

Example 1

A solution of 100 mg of the polysaccharide in 30 ml of water is cooled to 2° C. The solution is allowed to pass a 1.6×7 cm column with Dowex 50-8X (H+) (200-400 mesh) at a rate of 2 ml/min. The column is washed with 20 ml water. To the eluate there is added 50 ml peroxide-free 1,3-dimethoxy ethane and 0.01 ml 1-butyl nitrite and the mixture is left at −20° C. for 24 hours. The reaction mixture is worked up by dialysis against distilled water and lyophilization.

Example 2

A solution of heparin (mucous, Kabi Vitrum) (1 g) in 300 ml water is cooled to 0° C. on an ice bath. Sodium nitrite 10 mg is added with stirring. Then acetic acid is added drop-wise (2 ml). The solution is allowed to stand under stirring for two more hours at 0° C. The reaction mixture is worked up by dialysis against distilled water and lyophilization.

PREPARATION OF SURFACES HAVING AFFINITY TOWARDS BLOOD

Example 3

Tubings of polyethylene were initially provided with a negative surface charge (sulfate groups) by treatment for 2 minutes with concentrated sulphuric acid containing 2 g/l of $KMnO_4$. After rinsing the tubings were exposed for 5 minutes to a 0.1% aqueous solution of a polymer cationic tenside (Polymin SN; BASF) at pH 9. After renewed rinsing the tubings were incubated with a solution of heparin diazotized as in Example 2 (20 mg/ml) (a) or 2 mg/ml (b) and sodium cyanoborohydride (0.5 mg/ml) in a phosphate buffer pH 7.0 for 24 hours at room temperature. The heparinized surface was finally carefully rinsed with water.

Carbazol test (ref. 9) showed that ∼10 μg heparin/cm² had been attached to the surface both in case a and in case b. The quantity of heparin which is available for interaction with protein was semi-quantitatively analyzed in the following manner. The measurement is based on the fact that thrombin is bound to heparin whereafter the quantity of surface-bound thrombin is measured by reaction (hydrolysis) of a thrombin specific substrate, S-2238 (Kabi Diagnostica) the rate of conversion of which can be simply established by spectrophotometry. In practice the measurement is performed by initially incubating the test surface for five minutes with bovine thrombin dissolved in 4% albumin solution to a final content of 20 NIH entities/ml. (NIH=National Institute of Health). Then the surface is carefully rinsed with saline and the remaining quantity thrombin is measured by incubation for 45 seconds with substrate S-2238 dissolved according to the directions of the manufacturer in a buffer solution at pH 8.4. The quantity of surface-bound thrombin and thereby also the quantity of available heparin is proportional to the quantity of substrate reacted. The value is measured in units of absorbance (un.ab.), where values lower than 0.100 un.ab. indicated insufficient binding capacity and values exceeding 0.500 un.ab. indicates satisfactorily high binding capacity of the surface-bound heparin.

The following values were obtained:
a. 1.340 un.ab.
b. 1.000 un.ab.

Measurement of the quantity of surface-bound thrombin may be utilized also for testing the functional non-thrombogenic properties of the surface. In this case the heparin surface (test surface) is initially incubated with human citrate plasma for 40 minutes for the purpose of providing to the surface a relevant protein adsorbate. The plasma is at the same time utilized to detect possible leakage of heparin. After plasma exposure the test surface is divided up into two groups. The first group is rinsed with only a physiologic saline, the other one also with defibrinogenated plasma (plasma freed from fibrinogen and thus non-coagulatable). The criteria for a non-thrombogenic surface are that the thrombin uptake which is measured under the same conditions as indicated above is at least 0.5 un.ab. in group I and less than 0.05 un.ab. in group II.

The following values were obtained:

|   | Group I | Group II |
|---|---------|----------|
| a | 0.860   | 0.010    |
| b | 0.800   | 0.005    |

The positive test result shows that the heparin surface by interaction with plasma proteins has the capacity of inhibiting thrombin, i.e. the surface shows biological activity. Measurement of heparin activity in the plasma rotating in the test tubings showed that less than 0.002 Iu heparin/cm$^2$ had been released from the surface, which is within the margin of error for this method.

Finally, the heparin surfaces were tested with regard to adhesion of thrombocytes. Tubings were rotated with fresh human citrate blood for 20 minutes and were then rinsed in a standardized manner with saline. Finally, ATP (adenosine triphosphate) was extracted from adhered thrombocytes with a buffer solution and the quantity of ATP was measured. The following results were obtained:

| Untreated polyethylene | $2357 \times 10^{-11}$ mmol ATP/cm$^2$ |
|---|---|
| a | $14 \times 10^{-11}$ mmol ATP/cm$^2$ |
| b | $22 \times 10^{-11}$ mmol ATP/cm$^2$ |

The test showed that the thrombocyte adhesion is strongly reduced compared to the corresponding untreated surface.

Example 4

Tubings of polyethylene (PE) were aminated by adsorption of polymer cation tenside, Polymin SN ® (BASF), in two different ways.

a: After sulfatization according to Example 3 the hoses were incubated for five minutes with a 0.1% aqueous solution of Polymin at pH 9.0 and were then rinsed carefully with water.

b: PE-hoses were treated without preceding sulfatization with a borate buffer solution pH 9 containing 0.5% glutardialdehyde and 0.0005% Polymin for five minutes at room temperature. After rinsing with water the tubings were incubated with an aqueous solution of dextran sulfate (Pharmacia Fine Chemicals) (1 mg/ml, 0.15M NaCl, 50° C., 5 min. pH 3.0) and were then carefully rinsed with water. The result of this treatment is that the surface is provided with negative charge. Finally, the tubings were incubated for five minutes with a 0.1% aqueous solution of Polymin at pH 9.0 and were carefully rinsed with water.

Tubings prepared according to a and b were then incubated for two hours at 55° C. with a phosphate buffer solution pH 3.9 containing 0.25 mg/ml of heparin diazotized as in Example 2 (mucous, Kabi Vitrum) and 0.025 mg/ml sodium cyanoborohydride. The treatment was terminated with careful water rinsing.

The heparinized tubings were then tested in the same manner as described in Example 3, the following results being obtained.

1. Thrombin uptake without preceding plasma exposure
   a. 1.100
   b. 1.990

2. Function test by measuring adsorption and inhibition of thrombin on heparin surface provided with plasma protein adsorbate.

|   | Group I | Group II |
|---|---------|----------|
|   | only saline rinsing | saline + defibrinogated plasma |
| a | 0.870 | 0.010 |
| b | 0.900 | 0.010 |

2. Test on thrombocyte adhesion

| Untreated PE | $2800 \times 10^{-11}$ mmol ATP/cm$^2$ |
|---|---|
| a | $11 \times 10^{-11}$ mmol ATP/cm$^2$ |
| b | $115 \times 10^{-11}$ mmol ATP/cm$^2$ |

The test shows that both a and b have satisfactorily low thrombocyte adhesion.

Example 5

PVC-tubing (Tygon S-50-HL Class VI having an inner diameter of 3 mm) was aminated for 24 hours in room temperature by treatment with a solution of 1.6-diaminohexane in ethanol (5 g/100 ml). The tubing was washed with (1) ethanol (1 l) and (2) (1 l) and was heparinized as in Example 3. The carbazol reaction (ref. 9) showed that ~3 μg heparin/cm$^2$ had been bound to the surface.

Measurement of thrombin uptake without preceding plasma exposure according to Example 3 resulted in 0.520 un.ab.

PREPARATION OF HEPARIN SEPHAROSE

Example 6

Suction dry Sepharose CL 4B (Pharmacia Fine Chemicals) (75 g) was oxidized with 0.2M $Br_2$ (115 mg). When all $Br_2$ had been consumed the gel was washed with distilled $H_2O$ (1 l). 1,6-Diaminohexane (25 g) dissolved in 50% $HOAc.H_2O$ to pH 6.4 and $NaBH_3CN$ (0.7 g) was added to the oxidized gel. The gel was shaken for 64 hours and then washed with dist. $H_2O$, 5% HOAc, 25, 50, 75 and 95% ethanol in $H_2O$, then dist. $H_2O$ (ca. 500 ml of each). Results: ~10 mole % ~7 percent by weight 1,6-diaminohexane is linked to the gel (analyzed by NMR in DCl) (ref. 10).

Suction dry hexandiamine gel (10 g)+500 mg of nitrite degraded heparin (mucous, Kabi Vitrum) as in Example 2+500 mg $NaBH_3CN$ in 0.2M phosphate buffer pH 7 (10 ml) was shaken for 4 days. The gel was washed with dist. $H_2O$, 1M NaCl dist. $H_2O$, 0.5 m NaAc pH 5, dist. $H_2O$ (~200 ml of each). Sulfur analysis (2.2%) showed that the gel contained ~22% heparin. The gel bound ~ double the quantity of AT/mole immobilized heparin as commercial heparin-Sepharose (Pharmacia Fine Chemicals AB).

PREPARATION OF PERMANENTLY ACTIVATED AT

Example 7

As in Example 1 nitrite degraded heparin (mucous, Kabi Vitrum) (10 mg, $M_w$ 2800) is fractionated on an AT-Sepharose column (ref. 11). The high-active fraction (~2 mg) was eluated from the column by increasing the ion strength (1M NaCl). Fragments together with $NaBH_3CN$ (5 mg) were added to AT (50 mg) in a molar proportion of 1.2:1 (heparin: AT) in 10 ml phosphate buffer (0.2M, pH 7.0). After 24 hours the mixture was concentrated to 2 ml and transferred onto a Sephadex G-100 (Pharmacia Fine Chemicals) column. The protein peak (35 mg) contained 0.3 moles of heparin fragments (calculated on $M_w$=2800) per mole AT and had an activity without extra heparin addition corresponding to 74% of the maximum. The protein fraction was purified on a heparin-Sepharose-column (Pharmacia Fine Chemicals) where non-reacted AT adheres. The fraction not adhering to the column (5.5 mg) contained 1.7 moles of fragments per mole of AT and had 100% of maximum activity. The activity sank to 85% in the presence of polybren; a reagent cleaving non-covalent AT-heparin complexes. The results showed that 85% of the protein fraction (~5 mg) contained heparin covalently bound to AT in such a manner as to permanently activate the protein. No doubt, the yields can be increased by using heparin fragments having optimum mole weights for activation and coupling.

PARTIAL N-DEACETYLATION OF POLYSACCHARIDES CONTAINING N-ACETYL GLUCOSAMINE ENTITIES

Example 8

Hyaluronic acid (100 mg) was dissolved in water (10 ml) and sodium hydroxide (4 g) was added. The solution was mixed with DMSO (50 ml) in a serum bottle, nitrogen gas was blown into the bottle which was then sealed. The mixture was heated on a water bath 100° C. and shaken at intervals. After 1 hour the mixture was poured into 50% acetic acid (15 ml) and was then dialyzed against (1) tap water and (2) distilled water. After lyophilization partially deacetylated polysaccharide (95 mg) was obtained.

Example 9

Dermatan sulfate (1 g) containing 2-amino-2-deoxy-N-acetyl glucosamine entities (N-acetyl-D-galacto- and glucopyranosyl entities) was dissolved in 30 ml hydrazine containing hydrazine sulfate (1.5 g). The mixture was heated for 0.5 hour to 105° C. in an ampoule. Then, the reagent was removed by vapourization under low pressure. The polysaccharide was dialyzed against (1) 10% acetic acid (1 l, over night) and (2) distilled water (5 l, over night).

BINDING OR DERMATAN SULFATE AND HYALURONIC ACID TO PLASTIC SURFACES

Example 10

Dermatan sulfate (50 mg), (gift from Ulf Lindahl), deacetylated as in Example 9 and diazotized as in Example 2, was dissolved in 5 ml phosphate buffer (0.2M, pH 7.0). To the resulting solution there was added $NaBH_3CN$ (5 mg) and the mixture is allowed to react with a polymine treated tubing as in Example 3. Colouring with toluidineblue showed that dermatan sulfate had been bound to the tubing.

The quantity of dermatan sulfate which is available for interaction with protein was semi-quantitatively indicated by measurement of surface-bound thrombin as in Example 3.

The following values were obtained:
(1) 0.820 un. ab.
(2) 0.890 un. ab.

Example 11

Hyaluronic acid, (Healon ®, Pharmacia AB) (50 mg) deacetylated as in Example 9 and nitrite-degraded as in Example 2, was allowed to react with a tubing as in Example 10, and colouring with acianblue showed that hyaluronic acid had been bound to the surface.

The quantity of surface-bound hyaluronic acid was analyzed with regard to surface-bound thrombin as in Examples 3 and 10.

The following values were obtained:
(1) 0.730 un.ab.
(2) 0.750 un.ab.

BINDING OF POLYSACCHARIDE TO 1,6-DIAMINOHEXANE

Example 12

Heparin (50 g), nitrite degraded as in Example 2 was dissolved in phosphate buffer 10 ml. A solution of 1,6-diaminohexane (100 mg) in water (5 ml) was adjusted to pH 7.0 (0.5M HCl) and added together with $NaBH_3CN$ (10 mg) to the heparin solution. After 4 hours the reaction mixture was dialyzed against (1) 10% acetic acid (2 l) and (2) distilled water (5 l). After concentration and lyophilization the coupling yield was analyzed with $^1H$-NMR in DCl (ref. 10). Result: the heparin contains 7.5 percent by weight of 1,6-diaminohexane.

Example 13

Dermatan sulfate (50 mg), N-deacetylated and nitrite-degraded as in Example 10, was coupled to 1,6-diaminohexane as in Example 12. The mixture was worked up and analyzed as in Example 12. Result: the dermatan sulfate contained 1 percent by weight of 1,6-diaminohexane.

Example 14

Chitosan (100 ml), N-deacetylated and nitrite-degraded as in Examples 9 and 10, respectively, was coupled to 1,6-diaminohexane as in Example 12. The mixture was worked up and analyzed as in Example 12. Result: The chitosan contained 0.5 percent by weight of 1,6-diaminohexane.

REFERENCES

1. U. Lindahl, MTP Int. Rev. Sci., Org. Chem. Ser. Two, 7 (1976) 283–312.
2. J. S. Brimacombe och J. M. Webber, Biochim. Biophys. Acta Library, Vol. 6. Elsevier, Amsterdam.
3. A. B. Foster and J. M. Webber, Adv. Carbohydr. Chem. 15 (1960), 371–393.
4. T. W. Barrowcliffe, E. A. Johnson and D. Thomas, Br. Med. Bull., 34 (1968), 143–150.
5. M. Miller-Andersson, H. Borg and L. O. Andersson, Thromb. Res., 5 (1974), 439–452.
6. B. Meyer, L. Thunberg, U. Lindahl, O. Larm and I. G. Leder. Carbohydr. Res., 88 (1981), C1–C4.
7. R. Larsson, Chemical Constitution and Biological Properties of a Heparinized Surface, Thesis, 1980, Department of Experimental Surgery, Karolinska Institutet, and Aminkemi AB, Stockholm och referenser i denna.
8. R. F. Borch, M. D. Bernstein and D. H. Durst, J. Am. Chem. Soc. 93 (1971) 2897–2904.
9. Z. Dische, Methods Carbohydr. Chem. 1 (1962) 481–482.
10. J. Rosengren, S. Påhlman, M. Glad, and S. Hjertén, Biochim. Biophys. Acta, 412 (1975) 51–61.
11. U. Lindahl, G. Bäckström, M. Höök, L. Thunberg, L. Å. Fransson and A. Linker, Proc. Natl. Acad. Sci. U.S.A., 76 (1979) 3198–3202.

I claim:

1. A process to produce by covalent binding conjugates of a substance containing a 2-amino-2-deoxyglycopyranosyl unit the $NH_2$-function of which in its most stable conformation is equatorially oriented, and a substrate containing a primary amino group, wherein said substance is selected from the group consisting of heparin, deacetylated dermatan sulfate, chitosan, and deacetylated hyaluronic acid, and wherein said substrate is selected from the group consisting of polyvinyl chloride, polyethylene, sepharose and antithrombin, comprising the following sequence of steps, degrading said substance by diazotation to form a substance fragment having a free terminal aldehyde group, reacting said fragment through its aldehyde group with the amino group of the substrate to form a Schiff's base, and reducing the base to a secondary amine.

2. A process according to claim 1, wherein the diazotation is performed in aqueous solution with an agent having the ability to form $NO^+$-ions.

3. A process according to claim 1 wherein the reaction of aldehydo and amino groups is performed in a reaction media selected from the group consisting of an organic solvent and an aqueous solution.

4. A process according to claim 1 wherein the reduction of the Schiffs base is performed with cyanoborohydride.

5. A conjugate comprising a 1-deoxy-2,5-anhydrohexitol unit which constitutes the terminal unit in a substance selected from the group consisting of heparin, deacetylated dermatan sulfate, chitosan, and deacetylated hyaluronic acid, which substance is covalently bound in the 1-position to an amino group associated with a substrate, wherein said substrate is selected from the group consisting of polyvinyl chloride, polyethylene, sepharose and antithrombin.

6. A conjugate according to claim 5 wherein the hexitol entity is a mannitol unit.

7. A conjugate according to claim 5 wherein the hexitol entity is a talitol.

8. A process according to claim 2 wherein the reaction of aldehydo and amino groups is performed in a reaction media selected from the group consisting of an organic solvent and an aqueous solution.

9. A process according to claim 2, wherein the agent has the ability to forming $NO^+$-ions in sodium nitrite or butyl nitrite.

* * * * *